United States Patent [19]

Tsuchiya et al.

[11] 4,434,104

[45] Feb. 28, 1984

[54] PREPARATION OF HIGH PURITY DI-LOWER ALKYL NAPHTHALENEDISULFONATES

[75] Inventors: Shuji Tsuchiya; Hisao Ikeda; Kenji Suzuki, all of Funabashi, Japan

[73] Assignee: Nissan Chemical Industries, Ltd., Tokyo, Japan

[21] Appl. No.: 387,605

[22] Filed: Jun. 11, 1982

[30] Foreign Application Priority Data

Jun. 17, 1981 [JP] Japan .................................. 56-93372
Jun. 24, 1981 [JP] Japan .................................. 56-98054

[51] Int. Cl.$^3$ .......................................... C07C 143/68
[52] U.S. Cl. ................................................. 260/456 P
[58] Field of Search ...................................... 260/456 P

[56] References Cited

PUBLICATIONS

Shiryaev et al., Chem. Abs., 76, 3500t, (1972).

Primary Examiner—Nicky Chan
Attorney, Agent, or Firm—Frishauf, Holtz, Goodman & Woodward

[57] ABSTRACT

Disclosed is an improved process for preparing di-lower alkyl naphthalenedisulfonyl by employing a naphthalenedisulfonate chloride and a stoichiometrically excess amount of an aliphatic alcohol and allowing them to react in the presence of an aqueous solution of an alkali. The improved process comprises treating the reaction product from said process with an alkali metal alcoholate and then washing the thus treated reaction product with water to obtain a highly pure product. Also disclosed is a process of limiting the formation of undesirable impurities arising from the reaction of said naphthalenedisulfonyl chloride and said aliphatic alcohol.

23 Claims, No Drawings

PREPARATION OF HIGH PURITY DI-LOWER ALKYL NAPHTHALENEDISULFONATES

This invention relates to a process for preparing with a high purity a di-lower alkyl naphthalenedisulfonate represented by the general formula (I):

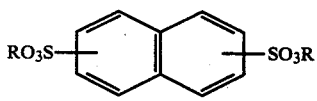
(I)

wherein R is a methyl or ethyl group and the substituent groups assume either 1,5- or 2,6-positions. This invention also relates to a process for limiting the formation of undesirable impurities arising from the reaction of a naphthalenedisulfonyl chloride represented by formula (II) shown below and an aliphatic alcohol having the general formula shown below.

More particularly, this invention relates to a process for preparing with a high purity and yield a di-lower alkyl naphthalenedisulfonate represented by the above general formula (I) by employing a naphthalenedisulfonyl chloride represented by the general formula (II):

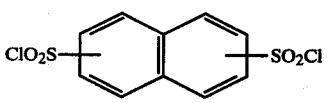
(II)

wherein the substituent groups assume either 1,5- or 2,6-positions
and a stoichiometrically excess amount of an aliphatic alcohol represented by the general formula: ROH, wherein R is a methyl or ethyl group, and causing them to undergo a reaction in the presence of an aqueous solution of an alkali, which process comprises removing any impurities from the resulting crude reaction product in the presence of a solvent.

In order to lower the content of impurities in the resulting reaction product and to carry out the purification step more advantageously, the preparation step of the crude di-lower alkyl naphthalenedisulfonate represented by the general formula (I) may be preferably carried out under the following conditions:

(a) Add the naphthalenedisulfonyl chloride and aqueous solution of an alkali, in portions, into the stoichiometrically excess amount of aliphatic alcohol;
(b) Maintain the chemical equivalent ratio of the alkali to naphthalenedisulfonyl chloride in the aliphatic alcohol below 1.1 along the entire course of their addition and adjust, upon completion of their addition, the above ratio to 1.0–1.2;
(c) In the course of adding the naphthalenedisulfonyl chloride and aqueous solution of the alkali in portions, ensure that a portion of the naphthalenedisulfonyl chloride be always added prior to the addition of its corresponding portion of the aqueous solution of the alkali; and
(d) Complete the addition of the aqueous solution of the alkali in a time period as short as feasible.

The compounds represented by the general formula (I) are excellent for use in the alkylation of organic compounds containing one or more active hydrogen atoms or in the conversion of tertiary amines into quaternary amines. They are thus useful as intermediate reaction products for the syntheses of pharmaceutically, agriculturally, and catalytically effective compounds. When employing them as intermediates for physiologically active substances, they are required to have an extremely high purity (i.e., at least 98%). However, it has been extremely difficult to obtain the compounds (I) with a high purity and yield from their corresponding (I) with a high purity and yield from their corresponding starting compounds (II) in accordance with conventional preparation processes. The process of this invention has overcome the drawbacks of such conventional processes and is capable of providing with a high purity and yield the compounds (I) from their starting compounds (II). The process of this invention is also superior in economy and ease in its practice. Therefore, the process of this invention is extremely advantageous for its practice on an industrial scale.

Impurities, which are generally contained in a di-lower alkyl naphthalenedisulfonate represented by the general formula (I) and obtained in accordance with a process commonly employed in the art, consist principally of the starting naphthalenedisulfonyl chloride of the general formula (II), a monosulfonyl chloride represented by the general formula (III) which is a reaction intermediate, and a disulfonic acid of the general formula (IV) which is a hydrolysis product:

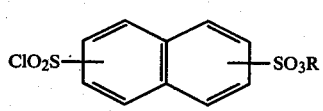
(III)

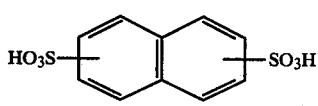
(IV)

wherein R has the same significance as defined above and the substituent groups assume the same positions as recited above.

Among such impurities, the compound (III) cannot be removed to any sufficient extent by the routinely-employed solvent recrystallization method due to its extreme similarity in solubility and melting point to the compound (I)-see, Comparative Examples 7 and 8.

The principal feature of the process according to this invention resides in the incorporation of a chemical treatment in the conventional solvent recrystallization method, whereby the compounds (II) and (III), which are impurities, are converted into the intended compound (I) and, on the other hand, water-soluble impurities are removed through a water-washing treatment thus leading to the production of the intended compound (I) having extremely high quality.

Another feature of the process according to this invention resides in that it facilitates the recirculation and reutilization of the recrystallization mother liquor owing to the fact that the mother liquor is substantially free of any impurities, thereby providing a purification yield higher than those available from any conventional methods and whereby the purification step operates as a closed system. Since it is not necessary to consider the difference in solubility between the compound (II) and compound (III) upon choosing a suitable solvent for recrystallization, more freedom will be enjoyed when selecting a proper recrystallization solvent. Furthermore, even if the compounds (II) and (III) are contained in higher concentrations, they may be successfully removed in accordance with the process of this invention by merely adding the chemical treatment agent in a somewhat higher proportion. Thus, the present process is extremely advantageous upon practicing it on an industrial scale.

Prerequisites of solvents which are useful in the practice of the process of this invention include (1) insolubility in water, (2) neutrality in nature and (3) high solubility for the compounds (I) and (II). As such solvents, halogenated hydrocarbons are suitable. Besides, ketone-type solvents such as methyl isobutyl ketone may also be employed. They are however not preferred since they are somewhat dissolved in water. It may also be feasible to use ester-type solvents such as propylene carbonate. However, they are expensive and thus disadvantageous from the economical viewpoint. On the other hand, sodium alcoholate or potassium alcoholate can be suitably used as the chemical treatment agent.

The process of one aspect this invention is made up of the following four steps:

First Step: A di-lower alkyl naphthalenedisulfonate, containing the compounds (II), (III) and (IV) as impurities, is dissolved in a chlorinated hydrocarbon solvent such as dichloromethane or trichloromethane and then the water content is removed thoroughly.

Second Step: An alcoholic solution of sodium alcoholate or potassium alcoholate is added to convert the compounds (II) and (III) into the compound (I). The alcoholate is added in such an amount as required stoichiometrically for its reactions with the sulfonyl chlorides and water.

Third Step: Water-soluble impurities are extracted with water.

Fourth Step: The intended product is obtained through recrystallization, filtration and drying.

The first to third steps are carried out at 50°–100° C., and preferably 60°–90° C. in order to increase the volumetric efficiency.

It is certainly desirous that the crude reaction product contains less impurities prior to effecting the above purification steps, as it leads to a saving of the alcoholate to be added. Accordingly, the present inventors have succeeded in completing a method for lowering the content of impurities in the crude reaction product compared with any conventional processes.

The synthesis of an alkyl ester of an aromatic sulfonic acid is generally carried out by mixing an aromatic sulfonyl chloride and a stoichiometrically excess amount of an alcohol and then dropping, as an agent for removing HCl, a stoichiometrically excess amount of concentrated aqueous solution of caustic soda. Since this process takes a long time period for the completion of the reaction, the saponification of the resulting ester tends to take place spontaneously and its yield tends to become lower as the reaction time goes on ["YUKI KAGOBUTSU GOSEI HO", Vol. 11, Page 112 (1959)].

Where a naphthalene derivative is used as the aromatic nucleus, the reaction tends to become more difficult to proceed smoothly due to its lower solubility in the reaction solvent [Bull. Soc. Chim. 45, 109 (1929)]. Particularly when dimethyl naphthalenedisulfonate is synthesized from naphthalenedisulfonyl chloride which is represented by the general formula (II) and contains two groups derived from sulfonic acid, both starting material and reaction product are solid. Since the starting material, intermediate and intended product have a low solubility in the reaction solvent, the reaction does not, in many instances, proceed uniformly throughout the reaction system. Depending on physical parameters such as the manner of incorporating reactants, scale of the reaction, extent of stirring and state of particle distribution, 20–50% of the starting materials and intermediate may be left in the final reaction system.

It is not easy to remove unreacted starting material and intermediate by causing them to undergo further reactions or by purifying the reaction product, because such an attempt tends to trigger the spontaneous hydrolysis of the resulting ester or the ester and intermediate are very close in their physical properties. Therefore, it is most important not to leave the intermediate unreacted in the reaction stage.

Twenty percent or more of unreacted substances will be allowed to remain when the reaction is carried out in any manner other than the process of this invention, for example, by dropping an aqueous solution of an alkali into a slurry mixture of the starting material and alcohol (see, Comparative Example 1). Moreover, this tendency becomes more remarkable as the scale of the reaction increases.

Lots of unreacted substances will also be left even when the starting material is added to the mixture of an alkali and alcohol (see, Comparative Example 2). Temperature control will be extremely difficult if the starting material and alkali are added at once into a stoichiometrically excess amount of alcohol, because it will induce the generation of lots of heat. It is preferable to conduct this reaction at temperatures as low as possible, since the saponification of the starting material and intended product will be accelerated as the temperature goes higher.

It may also be contemplated to conduct the esterification reaction in a homogeneous system by dissolving the starting material in a large amount of an inert organic solvent such as ethylene dichloride. However, it is indispensable to carry out the reaction in an anhydrous system in order to suppress the hydrolysis of the starting material or intended product in a uniform reaction system. It is also essential to use, as the alkylating agent, a costly sodium alcoholate in an amount greater than that required stoichiometrically. Thus, this process involves too many problems to practice it on an industrial scale. Alternatively, expensive pyridine may be used in place of an aqueous solution of an alkali. This process has, however, encountered problems for its application in the industry, including the recovery of pyridine.

The present inventors have carefully studied the above reaction with a view toward overcoming the drawbacks of the above-mentioned prior art processes. As a result, they have succeeded in obtaining the intended product with good reproducibility and substantially stoichiometrically by controlling the reaction under the following conditions:

(a) Add the starting material and alkali, in portions, into the excess alcohol. Lots of substances will be left unreacted if only one of the starting material and alkali is added in portions.

(b) Maintain the chemical equivalent ratio of the alkali to the starting material always below 1.1 or so along the course of their addition and adjust the same ratio to 1.0–1.2 at the end of their addition. When the above ratio is kept below 1.0, for example, at 0.9 in the course of their addition, particles are prohibited from coagulating and the reaction will thus be brought to completion when the amount of the alkali reaches or exceeds its stoichiometric amount in the final stage of the reaction. In other words, it is difficult, practically speaking, to maintain their chemical equivalent ratio always at 1.0 along the course of their addition and slight variations should thus be permitted. As a result of our detailed study, it has been found that a small amount of the alkali does not cause any problem at all in the course of their addition but abundance of the alkali induces coagulation of particles and tends to render the reaction incomplete. For example, 3–5% of the reactants will be left unreacted when they are added with a chemical equivalent ratio of 1.1. This will be increased to 5–8% when they are continuously added with a chemical equivalent ratio of 1.2. Since a longer reaction time is practically useless to reduce the amounts of unreacted reactants once they are confined to the interiors of coagulated reactants, it is important for the quantitative completion of the present invention to add both reactants in portions while maintaining their chemical equivalent ratio below 1.1, and preferably within a range of 0.9 to 1.05.

(c) Always add a portion of the starting material before its corresponding portion of the alkali when the starting material and aqueous solution of the alkali are added in portions. If a portion of the starting material is added subsequent to its corresponding portion of the alkali, particles of the starting material undergo coagulation and the reaction will never be brought to completion.

(d) Complete the addition of the alkali in a time period as short as possible. To cope with an abrupt heat generation which takes place here, it is necessary to adjust the amount of the alcohol to be used, stirring speed and cooling capacity. The time for the addition of the alkali is variable depending on the actual operational scale, but should preferably be not longer than 7 minutes.

(e) Carry out the reaction at temperatures below 20° C. Otherwise, the saponification of starting material and intended product will be accelerated. As the alkali usuable in the present invention, may be mentioned sodium hydroxide, potassium hydroxide or the like.

The present invention will hereinafter be described more specifically with reference to the following examples and comparative examples.

EXAMPLE 1

Into a 500 cc reaction vessel equipped with adding devices respectively containing 32.5 g (0.1 mole) of 1,5-naphthalenedisulfonyl chloride (II) and 18.3 g (0.22 mole) of a 48% aqueous solution of NaOH, was charged 200 cc of methanol. The methanol was cooled below 10° C. in an ice bath and stirred thoroughly. Out of the above 1,5-naphthalenedisulfonyl chloride of (II), 0.02 mole was added to the methanol and stirred for 5 minutes into a slurry which contained, 1,5-naphthalenedisulfonyl chloride in a well-dispersed state. Thereafter, 0.04 mole of the aqueous NaOH solution (chemical equivalent ratio=1) was incorporated and heat was liberated abruptly, thereby raising the temperature of the reaction system to 15°–20° C. In 5–10 minutes, the reaction system was cooled below 10° C. and the above portion-by-portion addition of the starting material and NaOH solution was resumed. The above portion-by-portion addition of the starting material and NaOH solution was repeated until they were added to their entirely. Upon completion of the reaction, the liquid reaction mixture was filtered and washed thoroughly with water. Upon drying the residue after filtration under reduced pressures, 31.4 g of dimethyl 1,5-naphthalenedisulfonate was obtained as white powder. Its high-speed liquid chromatographic analysis indicated that is purity was 98.5% and the remaining 1.5% was the following monosulphonyl chloride:

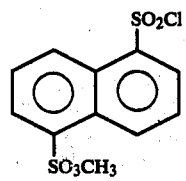

Their yields are as follows:

| Dimethyl 1,5-naphthalenedisulfonate | 98% |
|---|---|
| Monosulfonyl chloride | 1.5% |

EXAMPLE 2

The procedure of Example 1 was repeated on a scale 10 times that of Example 1.

Into a 5-liter reaction vessel equipped with adding devices containing respectively 325 g (1.0 mole) of 1,5-naphthalenedisulfonyl chloride (II) and 183 g (2.2 moles) of a 48% aqueous solution of NaOH, were charged 2 liters of methanol. The methanol was cooled below 10° C. on an ice bath. One fifth of the starting compound (II) was then added and thoroughly agitated, followed by an addition of a stoichiometric amount of the aqueous NaOH solution. Heat was generated abruptly and the temperature of the reaction system jumped to 15°–20° C. After the heat generation had stopped and the reaction system had been cooled again below 10° C., a similar procedure was repeated 4 times until the compound (II) and aqueous NaOH solution were added in their entirety. The resultant reaction mixture was filtered, washed with water, and dried into 312 g of crude white crystalline substance. As a result of its analysis by high-speed liquid chromatography, it was revealed that the white substance contained 98.5% of dimethyl 1,5-naphthalenedisulfonate and 1.5% of the above-mentioned monosulfonyl chloride. It had a melting point of 201°0 C. No substantial difference was observed on the yield due to the scale of the reaction.

| Yield: | Dimethyl 1,5-naphthalenedisulfonate | 97.5% |
|---|---|---|
|  | Monosulfonyl chloride | 1.5% |

EXAMPLE 3

The procedure of Example 1 was repeated except than 2,6-naphthalenedisulfonyl chloride was used in lieu of 1,5-naphthalenedisulfonyl chloride. Dimethyl 2,6-naphthalenedisulfonate was obtained with a yield of 98%.

EXAMPLE 4

The procedure of Example 1 was followed except for the employment of ethanol instead of methanol. Diethyl 1,5-naphthalenedisulfonate was obtained with a yield of 97%.

EXAMPLE 5

A reaction was carried out in the same manner as in Example 1 except that a concentrated aqueous KOH solution was used in place of the 48% aqueous solution of NaOH. Dimethyl 1,5-naphthalenedisulfonate was obtained with a yield of 98%.

COMPARATIVE EXAMPLE 1

Into a 1-liter reaction vessel, were charged 400 cc of methanol and 65 g (0.20 mole) of 1,5-naphthalenedisulfonyl chloride. They were maintained below 10° C. in an ice bath. While stirring them within a temperature range of 10°–20° C., 36.6 g (0.44 mole) of a 48% aqueous solution of NaOH was dropped over 30 minutes. The reaction mixture was allowed to undergo a reaction at 20° C. for an additional 4 hours. The reaction product was filtered, washed with water and then dried into a mixture. The yield of dimethyl 1,5-naphthalenedisulfonate was 73% whereas that of the monosulfonyl chloride was 23%. Compared with Examples 1–5, the yield of dimethyl 1,5-naphthalenedisulfonate in the present comparative example was lower.

COMPARATIVE EXAMPLES 2-5

The procedure of Example 1 was followed except that the compound (II) and NaOH solution were added in each of the following manners A, B, C and D and the reaction mixture was allowed to undergo a reaction at 20° C. for 1 hour after the completion of their addition. Results are shown in Table 1.

(A) 1,5-Naphthalenedisulfonyl chloride was added in the course of 30 minutes into a liquid mixture of methanol and a 48% aqueous NaOH solution;

(B) 0.04 Mole of 1,5-dinaphthalenedisulfonyl chloride was added into methanol and, 5 minutes later, 0.104 mole of a 48% aqueous NaOH solution was incorporated. This portion-by-portion addition was repeated 4 times.

(C) Into methanol, 0.04 mole of 1,5-dinaphthalenedisulfonyl chloride was added and, five minutes later, a stoichiometric amount of a 48% aqueous NaOH solution was added over 15 minutes. This portion-by-portion addition was repeated an additional 4 times. In total, 0.44 mole of NaOH was added.

(D) Into methanol, 0.08 mole of a 48% aqueous NaOH solution was added and, 5 minutes later, 0.04 mole of 1,5-naphthalenedisulfonyl chloride was added, followed by stirring the mixture for 10 minutes. This portion-by-portion addition was repeated an additional 4 times. In total, 0.44 mole of NaOH was added.

TABLE 1

| Comp. Ex. | Manner of Addition | (II)[1] | 48% Aqueous NaOH Soln. | Methanol | Reaction Temp. | Yield (I)[2] | Mono Sulfonyl Chloride |
|---|---|---|---|---|---|---|---|
| 2 | A | 0.20 mole | 0.44 mole | 400 cc | 10–20° C. | 58 | 40 |
| 3 | B | 0.20 mole | 0.52 mole | " | 10–20° C. | 90 | 8 |
| 4 | C | 0.20 mole | 0.44 mole | " | 10–20° C. | 93 | 5 |
| 5 | D | 0.20 mole | 0.44 mole | " | 10–20° C. | 60 | 37 |

Note:
[1] (II) ... 1,5-naphthalenedisulfonyl chloride
[2] (I) ... dimethyl 1,5-naphthalenedisulfonate As shown in Table 1, the yield of dimethyl 1,5-naphthalenedisulfonate was lower in each of the above comparative examples than its corresponding figures in Examples 1–5.

EXAMPLE 6

Into a 10-liter reaction vessel, were charged 310 g of the crude white crystalline substance obtained in Example 2 and 6.7 liters of dichloroethane. The water content in the system was reduced to 0.02 wt.% by azeotropic drying distillation and about 10 g of a 28% methanol solution of sodium methylate was thereafter added at about 60° C. so as to convert the monosulfonyl chloride, an impurity, into dimethyl 1,5-naphthalenedisulfonate. Water-soluble impurities were then removed by washing the reaction mixture once with water. Dimethyl 1,5-naphthalenedisulfonate was recrystallized from dichloroethane, collected through filtration and then dried, thereby obtaining 295 g of crystalline dimethyl 1,5-naphthalenedisulfonate having a purity of 99.9% or higher (melting point: 205° C.).

EXAMPLE 7

Similar to Example 2, 325 g (1.0 mole) of 1,5-naphthalenedisulfonyl chloride (II) and 200 g (2.4 moles) of a 48% aqueous NaOH solution were placed in their respective adding devices which were in turn provided with a 5-liter reaction vessel. Two liters of methanol were then charged into the reaction vessel and cooled below 5° C. in an ice bath. One fifth of the compound (II) was added and agitated well and, upon an addition of one fifth of the aqueous NaOH solution (chemical equivalent ratio: 1.2), heat was generated abruptly and the temperature of reaction system went up to 15°–20° C.

When the heat generation stopped and the temperature dropped below 10° C. the above procedure was repeated four times until all the compound (II) and aqueous NaOH solution had been added. The resulting reaction mixture was filtered, washed with water and then dried into 312 g of a crude white crystalline substance. Its high-speed liquid chromatographic analysis indicated that the substance contained 92% of dimethyl 1,5-naphthalenedisulfonate and 8% of the monosulfonyl chloride.

Using 310 g of the thus-obtained crude crystalline substance, the procedure of Example 6 was followed (30 g of a 28% methanol solution of sodium methylate was used). As a result, 294 g of crystalline dimethyl 1,5-naphthalenedisulfonate was obtained with a purity of 99.8% or higher.

EXAMPLE 8

The procedure of Example 2 was repeated except that 2,6-naphthalenedisulfonyl chloride was used in place of 1,5-naphthalenedisulfonyl chloride, resulting in the provision of crude crystalline dimethyl 2,6-naphthalenedisulfonate containing 2% of the monosulfonyl chloride. Using 310 g of the crude crystalline product, the procedure of Example 6 was repeated (10 g of a 28% methanol solution of sodium alcoholate was used). As a result, 294 g of crystalline dimethyl 2,6-naphthalenedisulfonate of a purity of at least 99.9% was obtained.

EXAMPLE 9

The procedure of Example 2 was followed except for the employment of ethanol in lieu of methanol, leading to crude crystalline diethyl 1,5-naphthalenedisulfonate which contained 2% of the monosulfonyl chloride. Using 310 g of the crude crystalline product, the procedure of Example 6 was applied (10 g of a 28% ethanol solution of sodium ethylate was used). As a result, 295 g of crystalline diethyl 1,5-naphthalenedisulfonate of a purity of 99.9% or higher was obtained.

EXAMPLE 10

The procedure of Example 6 was applied to 300 g of the crude crystalline substance (a mixture of 61.2% dimethyl 1,5-naphthalenedisulfonate and 38.7% of the monosulfonyl chloride) obtained in accordance with the process employed in Comparative Example 5. The 28% methanol solution of sodium methylate was used in an amount of 96.8 g. As a result, 286 g of crystalline dimethyl 1,5-naphthalenedisulfonate of a purity of 99.8% or higher was obtained.

COMPARATIVE EXAMPLE 6

Into a 1-liter reaction vessel, were charged 31.0 g of the crude crystalline dimethyl 1,5-naphthalenedisulfonate obtained in Example 2 and 670 cc of dichloroethane. The former was dissolved at 70° C. in the latter. About 500 cc of dichloroethane was caused to evaporate under reduced pressures and the residue was cooled to deposit 0° C. to a white crystalline product. It was then collected through filtration and dried to give 27.3 g of white crystalline dimethyl 1,5-naphthalenedisulfonate of a purity of 99.2%. The remaining 0.8% consisted of the monosulfonyl chloride, an impurity.

COMPARATIVE EXAMPLE 7

The procedure of Comparative Example 6 was repeated using 31.0 g of the crude crystalline product obtained in Example 7 in place of the crude crystalline substance obtained in Example 2, resulting in the production of 26.3 g of white crystalline dimethyl 1,5-naphthalenedisulfonate of a purity of 97.0%. The remaining 3% consisted of the impurity, monosulfonyl chloride.

We claim:

1. In a process for preparing a di-lower alkyl naphthalenedisulfonate of the formula:

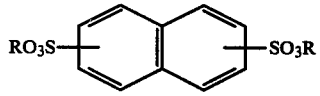

wherein R is selected from a methyl group and an ethyl group, said sulfonate groups being in either the 1,5- or 2,6-position,
by reacting a naphthalenedisulfonyl chloride of the formula:

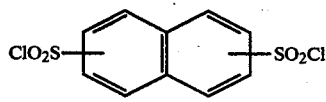

wherein the substituent groups are in either the 1,5- or 2,6-position,
and a stoichiometrically excess amount of an aliphatic alcohol of the formula:

ROH in the presence of an aqueous alkali solution, the improvement comprising removing water from the reaction system, treating the reaction product with an alkali metal alcoholate of the formula:

ROM wherein M is selected from a sodium atom and a potassium atom, in the presence of a solvent and then washing the treated reaction product with water.

2. The process according to claim 1, wherein said solvent is a halogenated hydrocarbon.

3. The process according to claim 2, wherein the halogenated hydrocarbon is selected from dichloromethane and dichloroethane.

4. The process according to claim 1, wherein the alkali metal alcoholate is selected from sodium methylate and sodium ethylate.

5. The process according to claim 1, wherein the alkali metal alcoholate is selected from potassium methylate and potassium ethylate.

6. The process according to claim 1, wherein the steps of treating the reaction product with an alkali metal alcoholate in the presence of a solvent and washing the thus treated product with water are conducted at a temperature of between 50° and 100° C.

7. The process according to claim 1, further comprising dissolving the reaction product in a chlorinated hydrocarbon solvent, removing water from the reaction system, treating the reaction product with a stoichiometric amount of an alkali metal alcoholate selected from the group consisting of sodium methylate, sodium ethylate, potassium methylate and potassium ethylate, and extracting water-soluble impurities with water.

8. The process according to claim 1, further comprising treating the reaction product with said alkali metal alcoholate in the presence of said solvent to obtain a liquid reaction mixture, filtering the reaction mixture to obtain a filtered product, washing the filtered product with water and drying said filtered product to obtain substantially pure di-lower alkyl naphthalenedisulfonate, said steps of filtering, washing and drying being conducted at a temperature between 60° and 90° C.

9. The process according to claim 6, wherein said solvent is selected from dichloromethane and dichloromethane, and said alkali metal alcoholate is selected from sodium methylate, sodium ethylate, potassium methylate and potassium ethylate.

10. A process for preparing a di-lower alkyl naphthalenedisulfonate of the formula:

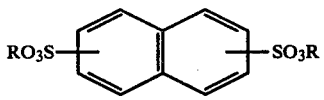

wherein R is selected from a methyl group and an ethyl group, said sulfonate groups being in either the 1,5- or 2,6-position, comprising adding a naphthalenedisulfonyl chloride of the formula:

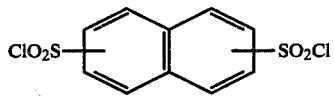

and an aqueous alkali solution in portions to a stoichiometrically excess amount of an aliphatic alcohol of the formula:

ROH wherein each portion of said chloride being added to said aliphatic alcohol prior to the corresponding portion of said aqueous alkali solution, and wherein the chemical equivalent ratio of said alkali to said chloride is maintained below 1.1, and adjusting the chemical equivalent ratio is between 1.0 and 1.2 upon completion of the addition of said portions.

11. The process according to claim 10, wherein the addition of the aqueous alkali solution is completed within seven minutes.

12. The process according to claim 10, wherein the addition of said chloride and said aqueous alkali solution is conducted at a temperature of less than 20° C.

13. The process according to claim 10, wherein the chemical equivalent ratio of said alkali to said chloride is maintained at between 0.9 and 1.05.

14. The process according to claim 10, wherein the aqueous alkali solution is selected from sodium hydroxide and potassium hydroxide.

15. The process according to claim 11, wherein the addition of said chloride and said aqueous alkali solution is conducted at a temperature of less than 20° C. and wherein the chemical equivalent ratio of said alkali to said chloride is maintained at between 0.9 and 1.05.

16. The process according to claim 10, further comprising removing water from the reaction system, treating the reaction product with an alkali metal alcoholate of the formula ROM wherein M is selected from a sodium atom and a potassium atom in the presence of a solvent and washing the treated reaction product with water.

17. The process according to claim 16, wherein said solvent is a halogenated hydrocarbon.

18. The process according to claim 17, wherein said halogenated hydrocarbon is selected from dichloromethane and dichloroethane.

19. The process according to claim 16, wherein the alkali metal alcoholate is selected from sodium methylate, sodium ethylate, potassium methylate and potassium ethylate.

20. The process according to claim 16, wherein the steps of treating the reaction product with an alkali metal alcoholate in the presence of a solvent and washing the thus treated product with water are conducted at a temperature of between 50° and 100° C.

21. The process according to claim 16, further comprising dissolving the reaction product in a chlorinated hydrocarbon solvent, removing water from the reaction system, treating the reaction product with a stoichiometric amount of an alkali metal alcoholate selected from sodium methylate, sodium ethylate, potassium methylate and potassium ethylate and extracting water-soluble impurities with water.

22. The process of claim 16, further comprising treating the reaction product with said alkali metal alcoholate in the presence of said solvent to obtain a liquid reaction mixture, filtering the reaction mixture to obtain a filtered product, washing the filtered product with water and drying said filtered product to obtain substantially pure di-lower alkyl naphthalenedisulfonate, said steps of filtering, washing and drying being conducted at a temperature between 60° and 90° C.

23. The process according to claim 20, wherein said solvent is selected from dichloromethane and dichloroethane, and said alkali metal alcoholate is selected from sodium methylate, sodium ethylate, potassium methylate and potassium ethylate.

* * * * *